(12) United States Patent
Andre et al.

(10) Patent No.: US 9,078,838 B2
(45) Date of Patent: Jul. 14, 2015

(54) COSMETIC OR DERMATOLOGICAL COMPOSITIONS COMPRISING A MIXTURE OF ESSENTIAL OILS, AND ITS USES THEREOF, PARTICULARLY FOR THE CARE OF SENSITIVE OR SENSITIZED SKIN

(75) Inventors: Patrice Andre, Neuville aux Bois (FR); Isabelle Renimel, Trainore (FR); Francine Joly, Paris (FR)

(73) Assignee: LVMH Recherche, Saint Jean De Braye (FR)

( * ) Notice: Subject to any disclaimer, the term of this patent is extended or adjusted under 35 U.S.C. 154(b) by 784 days.

(21) Appl. No.: 12/553,200

(22) Filed: Sep. 3, 2009

(65) Prior Publication Data

US 2010/0080861 A1    Apr. 1, 2010

(30) Foreign Application Priority Data

Sep. 5, 2008   (FR) ...................... 08 55994

(51) Int. Cl.
| | | |
|---|---|---|
| A61K 36/00 | (2006.01) | |
| A61K 36/28 | (2006.01) | |
| A61K 8/92 | (2006.01) | |
| A61Q 19/00 | (2006.01) | |
| A61Q 1/02 | (2006.01) | |
| A61Q 1/10 | (2006.01) | |

(52) U.S. Cl.
CPC .............. *A61K 8/922* (2013.01); *A61Q 19/005* (2013.01); *A61Q 1/02* (2013.01); *A61Q 1/10* (2013.01)

(58) Field of Classification Search
None
See application file for complete search history.

(56) References Cited

U.S. PATENT DOCUMENTS

| | | | |
|---|---|---|---|
| 2004/0258783 A1* | 12/2004 | Millou et al. .................. | 424/778 |
| 2009/0130220 A1* | 5/2009 | Johnson .......................... | 424/539 |
| 2010/0080861 A1 | 4/2010 | Andre | |

FOREIGN PATENT DOCUMENTS

| | | |
|---|---|---|
| DE | 10041700 A1 * | 3/2002 |
| KR | 2003046949 A * | 6/2003 |

OTHER PUBLICATIONS

Vogl et al. "Hemp (*Cannabis sativa* L.) as a Resource for Green Cosmetics" Journal of Industrial Hemp, vol. 9(1) 2004.*
Hahessy et al. "Urine Cannabinoids and Usage of Legal Hemp Products" Clinical Toxicology 37(4), 1999, p. 515.*
The Columbus Foods Web Store Web Page, http://web.archive.org/web2008123210518/http:/www.soaperschoice.com/soapoils/hempoil.html.*
Hahessy et al, ("Urine Cannabinoids and Usage of Legal Hemp Products", Clinical Toxicology, 37(4), 515 (1990).)).*
Renimel et al, ("Identification of selective combinations of essential oils with anti-inflammatory effects, in biological in-vitro tests providing proof of their clinical efficacy," IFSCC (24th Congress 2006, Osaka, Japan), 3 pages)).*
Mediavilla et al. 1997, "Essential oil of *Cannabis sativa* L. strains", Journal of the international Hemp Association 4(2):80 -82.*
Hosoi, "Stress and the skin," International Journal of Cosmetic Science, 2006, 28, pp. 243-246.
Morizot et al., "Sensitive Skin: Analysis of Symptoms, Perceived Causes and Possible Mechanisms," Cosmetics and toiletries, 2000, 115 (11), pp. 83-89.
Renimel et al., "Identification of selective combinations of essential oils with anti-inflammatory effects, in biological in vitro tests providing proof of their clinical efficacy," IFSCC(24th IFSCC Congress 2006, Osaka, Japan), 3 pages.
Slominski et al., "Cutaneous Expression of CRH and CRH-R: Is There a Skin Stress Response System?", NY Acad. Sci., 1999, 885, pp. 287-311.

* cited by examiner

*Primary Examiner* — Chris R Tate
*Assistant Examiner* — Deborah Davis
(74) *Attorney, Agent, or Firm* — Baker & Hostetler LLP

(57) ABSTRACT

The present invention relates to cosmetic or dermatological compositions comprising a combination of a cannabis essential oil substantially free of cannabinoids and a helichrysum essential oil, and to their uses thereof, particularly for the care of sensitive or sensitized skin.

17 Claims, No Drawings

COSMETIC OR DERMATOLOGICAL COMPOSITIONS COMPRISING A MIXTURE OF ESSENTIAL OILS, AND ITS USES THEREOF, PARTICULARLY FOR THE CARE OF SENSITIVE OR SENSITIZED SKIN

CROSS REFERENCE TO RELATED APPLICATIONS

This application claims the benefit of French Patent Application No. 0855994, filed Sep. 5, 2008, the entirety of which is incorporated herein.

TECHNICAL FIELD

The present invention relates to new cosmetic compositions comprising a mixture of essential oils, as well as uses thereof, particularly for the care of sensitive or sensitized skin.

BACKGROUND

For centuries, essential oils have been the subject of both cosmetic and therapeutic uses. There is much information in the literature concerning their biological activities, derived for the most part from traditional remedies. Nevertheless, there are few studies providing proof of their activities by means of biological tests and confirming their clinical activities.

The paper entitled "Identification of selective combinations of essential oils with anti-inflammatory effects, in biological in vitro tests providing proof of their clinical efficacy", published in the journal of the IFSCC (24th IFSCC Congress 2006, Osaka, Japan), gives the results of the effects obtained using ten essential oils, from three different origins, with regard to their anti-inflammatory properties. This article shows that the essential oils studied exhibit anti-inflammatory activities in vitro. The study carried out by the author identified four groups classed according to their inhibitory effects on the production of the inflammation mediators LTB4, 11-8 or PG E2.

Moreover, the same study shows that a number of these oils prove to be potent elastase inhibitors.

This paper, however, is not concerned at all with the effect of these essential oils on the release of histamine under the action of the corticotropin-releasing hormone (CRH), an effect which underlies the present invention.

Sensitive skin is characterized by a tendency toward cutaneous hyperreactivity as compared to a normal skin subjected to the same stimulus, and in particular to an environmental stimulus.

The environmental stimuli which trigger or induce said reactions may be physical (UV radiation, temperatures, etc.), chemical (pollution, etc.), hormonal (menstrual cycle) or emotional (stress) (Morizot et al. Cosmetics and toiletries, 2000, 115 (11), pp. 83-89).

This hyperreactivity, like the signs of skin allergy, is manifested in stinging, redness, heat sensations, tingling or itching.

Consequently, compositions for the treatment of sensitive or sensitized skin are necessary.

SUMMARY

The present invention is directed to cosmetic or dermatological compositions combining a cannabis essential oil substantially free of cannabinoids, a helichrysum essential oil, and at least one cosmetically or dermatologically acceptable excipient compatible with topical application to the skin, lips or superficial body growths. Methods of using these compositions is also described.

DETAILED DESCRIPTION OF ILLUSTRATIVE EMBODIMENTS

The present invention provides new cosmetic or dermatological compositions comprising a combination of two essential oils, namely a cannabis essential oil and a helichrysum essential oil.

The invention is also directed to the use of this combinations of essential oils as an active agent in cosmetic or dermatological compositions intended for taking care of sensitive or reactive skin, or of normal skin which has been sensitized by a stressor, and particularly for the purpose of soothing said skin, and/or for reducing the signs of skin allergy, and/or for lowering the allergic potential or improving the tolerance of the composition when it is applied to the skin, lips or superficial body growths.

Lastly, the invention relates to a method of cosmetic care that comprises applying these compositions to the skin, lips or superficial body growths.

The present invention results from the finding that the mixtures of two particular essential oils, namely a cannabis essential oil and a helichrysum essential oil, allow significant reduction in the release of histamine as caused by corticotrophin-releasing hormone (CRH), even though each of these two oils taken separately has no inhibitory action at all.

This finding has led to the development of compositions comprising a combination of these two essential oils, said compositions exhibiting particularly advantageous anti-allergic properties. This combination of essential oils in a single composition proves advantageous for lowering the allergic potential of a composition associated with the presence of other constituents of said composition. This combination of essential oils thus allows the tolerance of a composition to be improved, more particularly that of a cosmetic or dermatological composition when it is applied to the skin.

Owing to the activity demonstrated by the inventors of the present invention, the compositions comprising this mixture of essential oils, referred to hereinafter as compositions of the invention, constitute new industrial products and prove to be particularly advantageous for the care of skin referred to as sensitive or reactive skin, for the care of normal skin which has been sensitized through the effect of a stress, or for reducing skin allergy phenomena.

The invention provides a cosmetic or dermatological composition combining a cannabis essential oil substantially free of cannabinoids, and in particular of psychoactive cannabinoid substances, and a helichrysum essential oil, further comprising at least one cosmetically or dermatologically acceptable excipient compatible with topical application to the skin, lips or superficial body growths.

The invention further provides for the use of a combination of essential oils as defined firstly above as an active agent in a cosmetic or dermatological composition which is compatible with topical application to the skin, lips or superficial body growths, or for preparing such a composition, said composition being intended:

for taking care of and/or for making up sensitive skin or reactive skin or normal skin which has been sensitized through the effect of a stress, particularly for the purpose of soothing said skin, and/or for reducing the signs of skin allergy, and/or for lowering the allergic potential or for improving the tolerance of said composition when it is applied to the skin, lips or superficial body growths.

The invention also provides a method of cosmetic care of the skin, particularly intended for the care of sensitive skin, reactive skin or normal skin which has been sensitized by a stress, which method comprises applying to the affected parts of the skin a composition as defined firstly above, for the purpose of obtaining a calming and soothing effect, with the consequent progressive provision of relaxed facial features, skin that is smoother and more toned, skin that is soothed and softer to the touch, a luminous and radiant complexion, and, moreover, leading possibly to a feeling of well-being.

Other features and advantages of the various aspects of the invention will emerge from the detailed description which follows.

The cannabis essential oil is advantageously a hemp (Cannabis sativa) essential oil.

The cannabis essential oil used according to the invention must be substantially free of cannabinoids, a group of chemical substances which activate the cannabinoid receptors that are present in the body.

The cannabis essential oil used according to the invention is more particularly substantially free of the cannabinoid substances which are known to be psychoactive, namely:

Δ9-tetrahydrocannabinol,
Δ8-tetrahydrocannabinol, and
cannabinol.

Cannabinol and its two aforementioned derivatives are molecules containing a dibenzopyran heterocycle and a pentyl chain. These molecules are lipophilic and are virtually insoluble in water.

In the context of the invention, the process used for preparing the cannabis essential oil is adapted such that the experimental conditions provide an essential oil which contains cannabinoid substances at most in trace amounts.

More specifically, the cannabis essential oil used in the context of the present invention is obtained by a hydrodistillation process which provides an essential oil substantially free of psychoactive substances. The reason for this is that the psychoactive substances that the plant might contain, especially those referred to above, are not entrained by the steam during distillation, owing to their lipophilic nature. Analyses show that only few traces, in insignificant amounts, of these substances remain.

The cannabis essential oil used in the compositions of the invention is obtained preferably from the whole plant, from the aerial parts, the plant and aerial parts being preferably seed-free, or from the flowering tops.

A cannabis essential oil obtained by hydrodistillation is free of the psychoactive molecules and is therefore ideally suited to the implementation of the present invention. This is because the psychoactive molecules that the plant might contain, particularly those referred to above, are not entrained by the steam during distillation, owing to their lipophilic nature. Analyses show that there are some traces of them remaining, but these traces are insignificant.

The cannabis essential oil used in the compositions of the invention is obtained preferably from the plant in the freshly harvested state.

The helichrysum essential oil used in the compositions of the invention is preferably obtained from the flowering tops or from the whole plant.

In one advantageous variant of the invention, the helichrysum essential oil is a Madagascan helichrysum (Helichrysum madagascariensis) or Italian helichrysum (Helichrysum italicum) essential oil.

The two essential oils used in the compositions of the invention may be those which already exist on the market and which meet the characteristics set out above. Raw materials of this kind are sold, for example, by the Rosier-Davenne company (Avignon, France).

The two essential oils combined for preparing the compositions of the invention may be used in proportions which vary very greatly. They are used in particular in mixtures in which the ratio of the concentrations of cannabis essential oils and helichrysum essential oils, respectively, may be between 99/1 and 1/99, preferably between 20/80 and 80/20, and, more preferably, about 50/50.

The total essential oil concentration of these two plant species combined within the composition according to the invention is between 0.001% and 1%, preferably between 0.01% and 0.5% and more preferably of the order of 0.1% by weight of the final composition.

The essential oils used according to the present invention, like all essential oils, are volatile aromatic extracts.

It may be of advantage, in order to enhance the desired effect, to introduce into the composition one or more agents intended to promote the volatilization of certain of the constituents of these essential oils (or of at least a fraction of said essential oils) at the time of application of the composition to the skin, or for enhancing their skin penetration.

These agents must of course be compatible with application to the skin.

As a means of volatilization, numerous agents can be used, in particular volatile alcohols, and especially ethanol or aqueous-alcoholic mixtures, for example a water/ethanol mixture.

As a means of skin penetration, it is possible in particular to use glycols or water/glycol mixtures.

Owing to their solubility in fatty substances, these helichrysum and cannabis essential oils are particularly well suited for incorporation into the fatty phases of cosmetic compositions, in particular in those intended for taking care for and/or for making up the skin, lips or superficial body growths.

These essential oils may be incorporated, for example, into the fatty phase of oil-in-water emulsions such as skincare creams.

Said fatty phase may also comprise a fatty excipient which is used for diluting these essential oils, and for facilitating their incorporation into the cosmetic composition.

This fatty excipient may be a vegetable oil, for example an oil obtained from jojoba, from coconut, from wheatgerm, from sweet almond, from olive or from apricot kernel, or a wax, or else a solid support such as silica, talc, porous or nonporous nylon powders, and micas, or any lamellar mineral substance.

Said composition of the invention may comprise at least one cosmetically acceptable excipient other than those mentioned above, which may in particular be selected from pigments, dyes, surfactants, rheological agents, perfumes, electrolytes, pH modifiers, antioxidants, and preservatives.

Furthermore, said composition may further comprise one or more other cosmetically acceptable active agents. In particular it may comprise as active agents other essential oils, molecules or extracts selected from substances having a skin-brightening activity; substances having a slimming activity; substances having a moisturizing activity; substances having a calming, soothing or relaxing activity; substances having activity stimulating the cutaneous microcirculation for the purpose of enhancing the radiance of the complexion, particularly of the face; substances having a seboregulatory activity for the care of greasy skin; substances intended for cleansing or purifying the skin; substances having anti-freeradical activity; substances intended for reducing or retarding the effects of aging of the skin, more particularly the formation of wrinkles, by activity promoting the maintenance of the structure of the skin and/or limiting the breakdown of the extracellular matrix of the surface layers of the dermis and the epidermis, and/or obtaining a protective, corrective or restructuring effect on the skin; and substances having an anti-inflammatory activity.

As set out above, the invention, and in particular the selection of the particular combination of essential oils, result from the discovery, by its inventors, of the unexpected effect of this combination in reducing the release of histamine.

The invention therefore relates, among other things, to the uses resulting from the remarkable properties of these combinations.

However, to the extent to which the combination of the two essential oils selected according to the invention has not yet been used, the invention also provides all of the applications of these combinations and the compositions comprising them.

Hence the invention provides in particular for the use of a combination of essential oils as defined above as an active agent in a cosmetic or dermatological composition compatible with topical application to the skin, lips or superficial body growths or for preparing such a composition, said composition being intended:

for taking care of and/or for making up sensitive skin or reactive skin or normal skin which has been sensitized through the effect of a stress, particularly for the purpose of soothing said skin, and/or for reducing the signs of skin allergy, and/or for lowering the allergic potential or for improving the tolerance of said composition when it is applied to the skin, lips or superficial body growths.

As emerges from the examples, the combination according to the invention allows a significant reduction in the release of histamine through the effect of CRH.

Consequently the invention likewise provides for the use of said combination for reducing the skin reactions induced by the release of histamine due to the secretion of CRH by the body through the effect of a stress.

The combination of the invention and the compositions comprising it are particularly useful in the care and treatment of skin reactions, and especially those of sensitive or reactive skin or of normal skin which has been sensitized by a stress, or in the treatment of the signs of skin allergies, these reactions and allergic signs being manifested, generally speaking, as stinging, heat sensations, redness, tingling or itching.

Another advantage of the compositions of the invention that is associated quite particularly with the volatile character of the essential oils in the combination of the invention is that of allowing penetration by the nasal route and of providing well-being.

Indeed it is known that there exists a close link between mental stress and cutaneous stress (*Stress and the skin, J., Hosoi, Int. J. Cosmet. Sci.,* 2006, 28:243-246). The link between the two is CRH, which is present in the skin and is produced subsequent to a stimulus of the hypothalamic-pituitary-adrenergic axis at the level of the hypothalamus (Slominski et al, *Ann. NY Acad. Sci.,* 1999, 885:287-311).

The volatilization of a fraction of these oils or of components of these essential oils at the time of topical application to the skin, lips or superficial body growths of the compositions of the invention allows them, by evaporation, to reach the nasal mucosa, and, by penetration thereof, to reduce the secretion of CRH at the central level and to impart well-being.

The newly discovered properties of the combination of the invention allow the compositions of the invention to be used in methods for cosmetic care of the skin and, quite particularly, in the cosmetic care of sensitive or reactive skin.

The compositions of the invention allow in particular, by application to the parts of the skin affected, the provision of a calming and soothing effect.

As set out above, the combination of the invention may also be used in compositions for making up the skin, lips and superficial body growths. It may in particular be used in the fatty phase of compositions in the form of oil-in-water emulsions.

Such uses in cosmetic compositions for care and/or makeup provide said compositions, therefore, with all of the advantages as set out above.

The examples which follow are given to illustrate the invention, without limiting its scope.

EXAMPLES

Example 1

Demonstration of the Inhibition of the Release of Histamine

Materials and Methods

To evaluate the activity of the combination of the invention on the release of histamine, which is an allergy mediator, a cutaneous stress model is reproduced ex vivo by applying a solution of CRH in the survival medium of explants of human skin.

1) Obtaining the Explants of Human Skin

Three explants of skin with a diameter of 8 mm are prepared from healthy human skin originating from surgical removal.

They are placed in 24-well plates and left to stand in an appropriate medium (MCDB 153, insulin, $CaCl_2$, gentamycin) for 24 hours.

2) Preparation of the Reactants

CRH (from Neosystem) is dissolved at a concentration of 231 μM in phosphate buffer (PBS) (pH 7.2).

The cannabis (*Cannabis sativa*) essential oil substantially free of cannabinoids, and the helichrysum (*Helichrysum madagascariensis*) essential oil, are obtained from Laboratoire Rosier-Davenne, France.

These oils, which are considered to be pure, are stored at 4° C.

First of all a 5% by weight (50 mg/ml) solution is prepared for each of the essential oils, in ethanol for the helichrysum oil and in DMSO for the cannabis oil.

The 5% by weight solutions are subsequently diluted at the time of use to 1/1000th in the survival medium of the explants, to give the different treatment solutions.

3) Application of the Treatments

The combination of cannabis and helichrysum essential oils is tested in the form of a treatment solution containing these two essential oils, each at a concentration of 0.005% by weight (50:50 ratio). Each essential oil is likewise tested on its own in the form of a 0.005% by weight treatment solution.

In each well the explant is at the surface of the survival medium. After these explants have stabilized, 35 μl of one of the treatment solutions is applied to the surface of the skin for each well. The treatment lasts for 24 hours.

Each concentration of each of the two essential oils or of the mixture is tested in triplicate.

4) Stimulation with CRH

After 24 hours of pretreatment with each of the helichrysum or cannabis essential oils, or with the mixture, the explants are transferred to a new 24-well plate containing 7.7 µM of CRH in a total volume of 300 µl of appropriate medium (MCDB 153, insulin, $CaCl_2$, gentamycin). The plate is placed in the oven for 2 hours.

5) Histamine Assay

Following stimulation, the supernatants are drawn off and the histamine is assayed by an ELISA method with the aid of a commercial kit (ICN).

Results

The assays are carried out in duplicate.
The results are given in the table below.

| Treatment | Histamine (ng/ml) | Conclusion of significance (Student, risk □ = 5%) |
|---|---|---|
| No stimulation (solvent control) | 15.3 +/− 1.0 | — |
| Stimulated with CRH, 7.7 µM (positive control) | 21.8 +/− 1.4 | Significant relative to the solvent control |
| Helichrysum 50 µg/ml | 21.8 +/− 1.4 | NS (>0.05) |
| Cannabis 50 µg/ml | 21.0 +/− 1.4 | NS (>0.05) |
| Mixture (50:50) ratio | 18.0 +/− 1.8 | S (≤0.05) |

NS: Not significant as compared to the positive control
S: Significant as compared to the positive control Conclusion CRH induces significant stimulation of the release of histamine by the cells of skin explants maintained in survival mode. Pretreatment with one or the other of the essential oils, helichrysum or cannabis, did not significantly reduce the release of histamine induced by CRH as compared to the positive control. On the other hand, the combination of the two essential oils in a single mixture (ratio 50/50) reduces the release of histamine in explants of human skin in a way which is statistically significant ($p<0.05$) as compared to the positive control.

Example 2

Emollient Emulsion for Sensitive Skin

| | |
|---|---|
| *Cannabis sativa* essential oil | 0.05% |
| *Helichrysum madagascariensis* essential oil | 0.05% |
| Excipients emulsified as oil in water (fatty alcohols, polyethoxylated fatty alcohols, vegetable oil, isopropyl palmitate, glycerol, gelling agent, preservatives, perfumes, ethanol, water) | qs 100% |

Example 3

Hypoallergenic Foundation

| | |
|---|---|
| *Cannabis sativa* essential oil | 0.05% |
| *Helichrysum madagascariensis* essential oil | 0.05% |
| Foundation base (fatty esters, squalane, soya lecithin, volatile silicone, propylene glycol, xanthan gum, sunscreen agent, pigments, preservatives, perfume, water) | qs 100% |

Example 4

Nonirritant Treatment Mascara for Sensitive Skin

| | |
|---|---|
| *Cannabis sativa* essential oil | 0.05% |
| *Helichrysum madagascariensis* essential oil | 0.05% |
| Ultramarine blue | 9.0% |
| Hexadecyl alcohol | 7.4% |
| Propylene glycol | 9.0% |
| Stearic acid | 11.3% |
| Glyceryl monostearate | 4.4% |
| Triethylamine | 3.6% |
| Preservative | 0.4% |
| Water | qs 100% |

What is claimed:

1. A cosmetic or dermatological composition for reducing histamine release comprising an effective amount of a combination of
   a cannabis essential oil obtained by a hydrodistillation process and being substantially free of cannabinoids, and
   a helichrysum essential oil; and
   at least one cosmetically or dermatologically acceptable excipient compatible with topical application to skin, lips or superficial body growths;
     wherein the ratio of the concentrations of the cannabis essential oil and the helichrysum essential oil is between 80/20 and 20/80.

2. The composition of claim 1, wherein said cannabis essential oil is a hemp (*Cannabis sativa*) essential oil.

3. The composition of claim 1, wherein the helichrysum essential oil is a Madagascan helichrysum (*Helichrysum madagascariensis*) or Italian helichrysum (*Helichrysum italicum*) essential oil.

4. The composition of claim 1, wherein said helichrysum essential oil is an oil obtained from the whole plant or from the plant flowering tops.

5. The composition of claim 1, wherein the combination is effective for
   treating sensitive skin, reactive skin, or normal skin that has been sensitized through the effects of a stress;
   reducing the signs of a skin allergy;
   lowering allergic potential; or
   improving the tolerance of the composition when it is applied to skin, lips, or superficial body growths.

6. A cosmetic or dermatological composition for reducing histamine release comprising an effective amount of a combination of
   a cannabis essential oil obtained by a hydrodistillation process and being substanitally free of cannabinoids, and
   a helichrysum essential oil; and
   at least one cosmetically or dermatologically acceptable excipient compatible with topical application to skin, lips, or superficial body growths;
     wherein the ratio of the concentrations of the cannabis essential oils and helichrysum essential oils is about 50/50.

7. The composition of claim 1, comprising at least one agent that, at the time of its application to the skin, promotes the volatilization of at least a portion of each of the essential oils and, optionally, an agent that promotes skin penetration of the essential oils, said agents being compatible with application to the skin.

8. The composition of claim 7, wherein said agent promoting volatilization is ethanol.

9. The composition of claim 1, the composition being in the form of an oil-in-water emulsion and further comprising a fatty phase into which said combination is introduced.

10. A method of inhibiting the release of histamine in skin, lips, or superficial body growths comprising
identifying skin, lips, or superficial body growths in need of histamine release inhibition;
applying to at least a portion of the skin, the lips or the superficial body growths, a cosmetic composition, compatible with topical application, comprising an effective amount of
a combination of a cannabis essential oil obtained by a hydrodistillation process and being substantially free of cannabinoids, and
a helichrysum essential oil,
wherein the ratio of the concentrations of the cannabis essential oil and the helichrysum essential oil is between 80/20 and 20/80.

11. The method of claim 10, wherein said combination is effective for treating sensitive skin, reactive skin, or normal skin which has been sensitized through the effects of a stress,
for reducing the signs of skin allergy,
for lowering the allergic potential,
for improving the tolerance of said composition when it is applied to the skin, lips, or superficial body growths, or
for reducing skin reactions caused by a stressor.

12. The method of claim 11, wherein the stressor results in the release of histamine.

13. The composition of claim 1, wherein the total concentration of helichrysum essential oils and of cannabis essential oils is between 0.01% and 0.5%, by weight of the composition.

14. The composition of claim 1, wherein the concentration of helichrysum essential oils is about 0.05%, by weight of the composition, and the concentration of cannabis essential oils is about 0.05%, by weight of the composition.

15. The composition of claim 1, wherein said cannabis essential oil is an oil obtained from the full plant, from the aerial parts, from the flowering tops, or from seed-free plants.

16. The method of claim 10, wherein the ratio of the concentrations of the cannabis essential oil and the helichrysum essential oil is about 50/50.

17. The composition of claim 6, wherein the total concentration of helichrysum essential oils and of cannabis essential oils is between 0.01% and 0.5%, by weight of the composition.

* * * * *